(12) United States Patent
Kuwano et al.

(10) Patent No.: US 8,672,915 B2
(45) Date of Patent: Mar. 18, 2014

(54) WEARING ARTICLE

(75) Inventors: Seiichi Kuwano, Kagawa (JP); Yoshio Ono, Kagawa (JP); Kyota Saito, Kagawa (JP)

(73) Assignee: Unicharm Corporation, Ehime (JP)

( * ) Notice: Subject to any disclaimer, the term of this patent is extended or adjusted under 35 U.S.C. 154(b) by 655 days.

(21) Appl. No.: 12/934,315

(22) PCT Filed: Jan. 19, 2009

(86) PCT No.: PCT/JP2009/050618
§ 371 (c)(1),
(2), (4) Date: Dec. 6, 2010

(87) PCT Pub. No.: WO2009/119139
PCT Pub. Date: Oct. 1, 2009

(65) Prior Publication Data
US 2011/0077609 A1    Mar. 31, 2011

(30) Foreign Application Priority Data

Mar. 27, 2008  (JP) ................................. 2008-084267

(51) Int. Cl.
*A61F 13/15*    (2006.01)
(52) U.S. Cl.
USPC ................... 604/392; 604/385.3; 604/385.31
(58) Field of Classification Search
USPC .................................. 604/392, 385.3, 385.31
See application file for complete search history.

(56) References Cited

U.S. PATENT DOCUMENTS

| | | | |
|---|---|---|---|
| 6,554,815 B1 | 4/2003 | Umebayashi | |
| 7,322,967 B2 * | 1/2008 | Kondo | ..................... 604/385.29 |
| 7,901,393 B2 * | 3/2011 | Matsuda et al. | ............... 604/392 |
| 2004/0108054 A1 | 6/2004 | Otsubo et al. | |
| 2004/0133180 A1 | 7/2004 | Mori et al. | |
| 2004/0243083 A1 | 12/2004 | Matsuda et al. | |
| 2005/0010186 A1 | 1/2005 | Otsubo et al. | |
| 2005/0098259 A1 | 5/2005 | Otsubo et al. | |
| 2006/0030831 A1 * | 2/2006 | Matsuda et al. | ............... 604/392 |
| 2009/0036860 A1 * | 2/2009 | Sugiyama et al. | ........ 604/385.29 |

FOREIGN PATENT DOCUMENTS

| | | |
|---|---|---|
| JP | 2001-478 A | 1/2001 |
| JP | 2002-273808 A | 9/2002 |
| JP | 2003-290284 A | 10/2003 |
| JP | 2003-339769 A | 12/2003 |
| JP | 2004-73427 A | 3/2004 |
| JP | 2006-525858 A | 11/2006 |
| WO | WO 03/077812 A1 | 9/2003 |
| WO | WO 2004/105665 A1 | 12/2004 |

OTHER PUBLICATIONS

International Search Report from corresponding PCT application No. PCT/JP2009/050618 dated Apr. 14, 2009, 4 pages.

* cited by examiner

*Primary Examiner* — Lynne Anderson
(74) *Attorney, Agent, or Firm* — Brinks Gilson & Lione

(57) ABSTRACT

A wearing article having front and rear waist belt members that include waist elastic members attached thereto and spaced one from another in a longitudinal direction Y. On non-contractile regions, these elastic members do not overlap graphics on respective heat-sealable sheets or exert contractile force thereon. The non-contractile regions are formed by leaving between inner and outer sheets as well as between inner and outer sheets not coated with adhesive in respective middles of the front and rear waist belt members as viewed in a transverse direction X and cutting the waist elastic members attached under tension in the respective middles of the waist belt members. Along the ends of the non-contractile regions on the side of the crotch member, the inner and outer sheets as well as the inner and outer sheets are respectively joined to each other by means of heat sealing technique so as to form the joint zones.

13 Claims, 3 Drawing Sheets

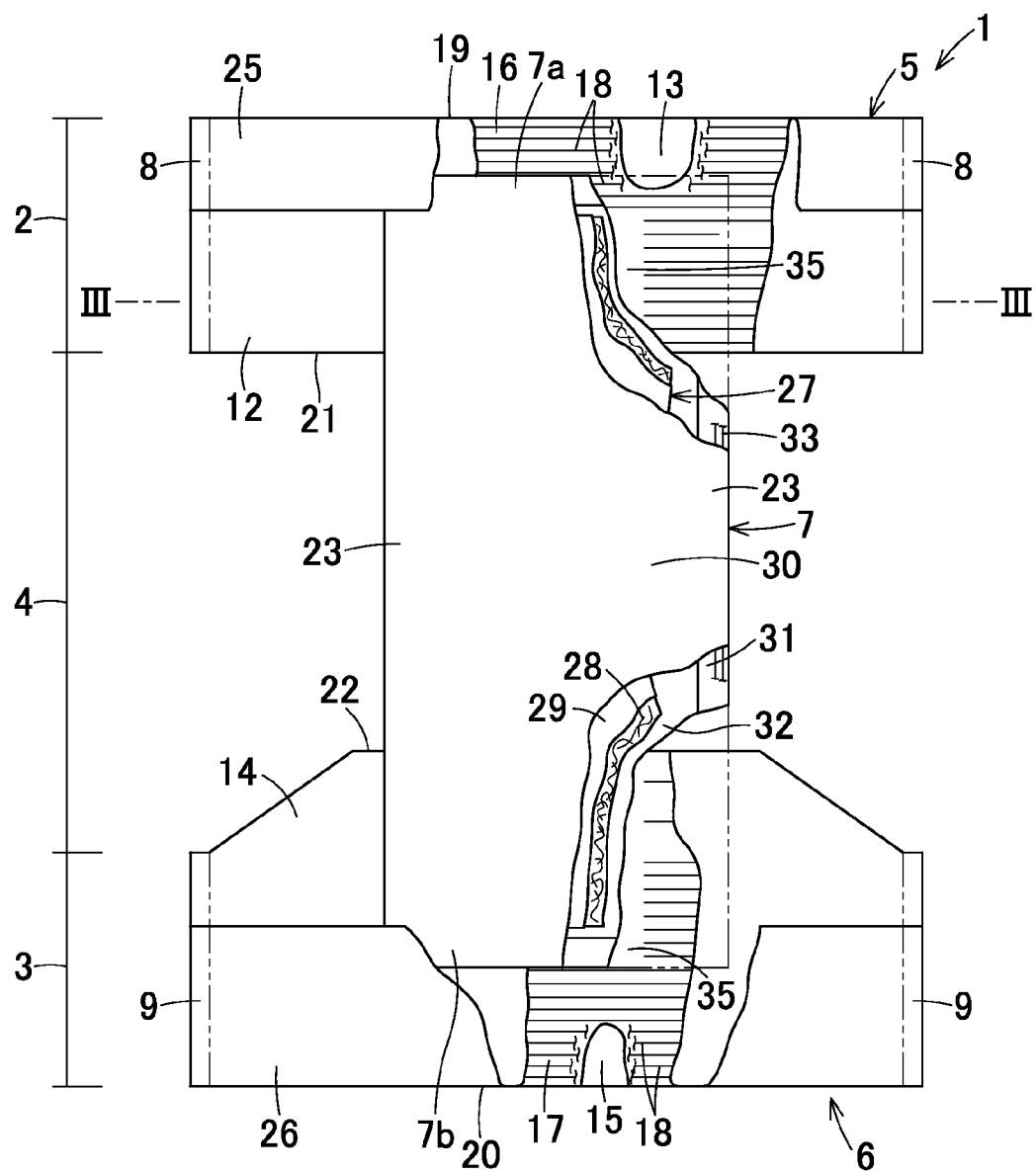

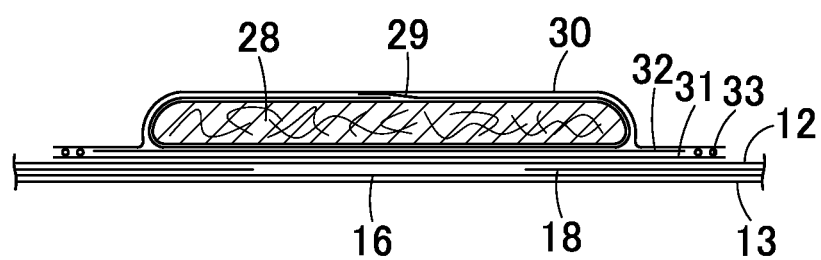

WEARING ARTICLE

RELATED APPLICATION

This application is a 35 U.S.C. §371 national phase filing of International Patent Application No. PCT/JP2009/050618, filed Jan. 19, 2009, through which and to which priority is claimed under 35 U.S.C. §119 to Japanese Patent Application No. 2008-084267, filed Mar. 27, 2008.

TECHNICAL FIELD

The present invention generally relates to wearing articles, particularly to wearing articles such as disposable diapers, toilet-training pants or incontinent briefs.

RELATED ART

Conventionally, pull-on type disposable diapers of having front and rear waist belts connected to each other by the intermediary of a liquid-absorbent structure have been known, for example, from JP 2006-525858 A. According to the disclosure of this JP 2006-525858 A, front and rear waist regions are respectively defined by the front and rear waist belts extending in a transverse direction and a crotch region is defined by the liquid-absorbent structure connecting the front and rear waist belts and extending in a longitudinal direction. Each of these front and rear waist belts comprises an inner layer sheet facing the wearer's skin, an outer layer sheet facing the wearer's garment, and a plurality of elastic members spaced one from another in the longitudinal direction from an upper end to a lower end of the waist belt and attached under tension between the inner and outer layer sheets so as to extend in the transverse direction. Each of the waist belts further comprises a patch printed with a graphic sandwiched between the inner and outer layer sheets.

In the diaper as has been described above, contractile force of the elastic members are inactivated in the graphic printed region so that the graphic may be clearly visible. More specifically, while the elastic members would be continuously bonded between the inner and outer layer sheets by adhesive, these elastic members are not bonded by adhesive in the region printed with the graphic and, in this adhesion-uncoated region, the elastic members are cut away. Consequentially, contractile force of the elastic members is not exerted on this adhesive-uncoated region and gathers or creases due to contraction of the elastic members would not make the graphic blurred.

PATENT DOCUMENT 1: JP 2006-525858 A

DISCLOSURE OF THE INVENTION

Problem to be Solved by the Invention

In the front and rear waist belts, adhesive applied between the inner and outer layer sheets bond not only the elastic members to the inner and outer sheets, but also the inner and outer sheets to each other. However, in the adhesive-uncoated region, the inner and the outer sheet are not bonded to each other and as a result, the inner and outer sheet open in the adhesive-uncoated region, and elastic members having been cut might stick out through such opening or the wearer's skin might be caught between the inner and outer layer sheets of such region.

In view of the problem as has been described above, it is an object of the present invention to provide a wearing article improved so that the front and rear waist belts is formed with non-contractile region but the elastic member would not stick out from this non-contractile region or the wearer' skin would not be caught by this non-contractile region as the prior art has been the case.

Measure to Solve the Problem

According to the present invention, there is an improvement in a wearing article having a longitudinal direction, a transverse direction, an inner side facing the wearer's skin, an outer side facing the wearer's garment, a front waist region, a rear waist region, a crotch region extending between the front and rear waist regions and connecting another in the longitudinal direction, waist belt members defining the front and rear waist regions, respectively, and a crotch member defining the crotch region partially inclusive of the front and rear waist regions, wherein the waist belt members include a pair of waist-line defining ends and a pair of ends on the side of the crotch member both pairs extending in the transverse direction and opposed to each other in the longitudinal direction, the waist belt members are provided under tension with a plurality of waist elastic members extending in the transverse direction and spaced one from another in the longitudinal direction and the waist belt members are partially formed with non-contractile regions free from contractile force of the waist elastic members.

The improvement according to the present invention is characterized in that the non-contractile region is formed along the waist-line defining ends of the waist belt members and/or the ends of the waist belt members on the side of the crotch member, and each of the waist belt members includes an inner sheet defining an inner side facing the wearer's skin and an outer sheet defining an outer side facing the wearer's garment wherein the waist line defining ends of the waist belt members and the ends of the waist belt members on the side of the crotch member both formed with the non-contractile regions are formed with joint zones along which the inner and outer sheets are joined together.

According to one preferred embodiment of the present invention, the non-contractile regions are formed in regions in which the waist belt members overlap the crotch member.

According to another preferred embodiment of the present invention, the waist belt members include heat-sealable sheets sandwiched between the inner and outer sheets, respectively, and the joint zones are formed by heat-sealing of the heat-sealable sheets.

According to still another preferred embodiment of the present invention, the heat-sealable sheets are formed on the side facing the wearer's garment thereof with graphics so as to make the graphics clearly visible through the outer sheets of the non-contractile regions.

According to yet another preferred embodiment of the present invention, the waist elastic members partially extend along the ends of the waist belt members on the side of the crotch member, the non-contractile regions are defined along the ends of the waist belt members on the side of the crotch member, and the waist elastic members are cut in the non-contractile regions.

According to further another preferred embodiment of the present invention, the crotch member includes a liquid-absorbent structure.

EFFECT OF THE INVENTION

The waist belt members respectively include the inner sheets facing the wearer's skin and the outer sheets facing the wearer's garment. The waist belt member are partially formed with the non-contractile regions free from contractible force of the waist elastic members and the waist-line defining ends of the waist belt members or the ends of the waist belt members on the side of the crotch member both formed with the non-contractile regions are formed with the joint zone. Thereby the inner and outer sheets are prevented from being opened in the non-contractile regions. In consequence, the waist elastic members having been cut can be prevented from sticking out and the wearer's skin can be prevented from being caught between the inner and outer sheets.

According to the embodiment wherein the non-contractile regions are formed in regions in which the waist belt members overlap the crotch member, it is assured that the contractile force of the waist elastic members is not exerted also upon the crotch member. As a result, the crotch member can be substantially prevented from getting wrinkles.

According to the embodiment wherein the waist belt members include heat-sealable sheets sandwiched between the inner and outer sheets, respectively, and the joint zones are formed by heat-sealing of the heat-sealable sheets, it is unnecessary to use adhesive or the other means to form the joint zones. In consequence, the manufacturing cost can be correspondingly reduced and the process of forming the joint zones can be simplified since a coating step for adhesive or the other means is eliminated.

According to the embodiment wherein the heat-sealable sheets are formed on the side facing the wearer's garment thereof with graphics so that said graphics would be able to be clearly visible through said outer sheets of said non-contractile regions. The graphics are formed on the non-contractile regions thereby gathers or creases would not make the graphic blurred.

According to the embodiment wherein the waist belt members partially extend along the ends of the waist belt members on the side of the crotch member, it is possible to improve the fit of the article to the wearer's body on the side of the crotch member and thereby bodily fluids can be prevented from leaking out. According to the embodiment wherein the waist elastic members are cut in the non-contractile regions, the contractile force of the waist elastic members is not exerted also on the region defined between the non-contractile regions and the ends of the waist belt members on the side of the crotch member. Thus none of wrinkles is formed between the waist belt members and the crotch member. The waist elastic members are cut in the non-contractile regions and thereby it is facilitated to inactivate the contractile force of the waist elastic members. The contractile force may be inactivated merely by but the waist elastic members after these elastic members have been attached. Therefore, even when the waist elastic members are partially attached along the ends of the waist belt members on the side of the crotch member, the non-contractile regions can be easily formed along these ends of the waist belt members on the side of the crotch member.

According to the embodiment wherein the crotch member includes a liquid-absorbent structure, the non-contractile regions overlap the liquid-absorbent structure. Consequentially, the liquid-absorbent structure can be prevented from getting wrinkles and leak of bodily fluids can be substantially prevented.

BRIEF DESCRIPTION OF THE DRAWINGS

[FIG. 2] Flatly developed plan view of the diaper.
[FIG. 3] Sectional view taken along the line III-III in FIG. 2.

Figure 1:
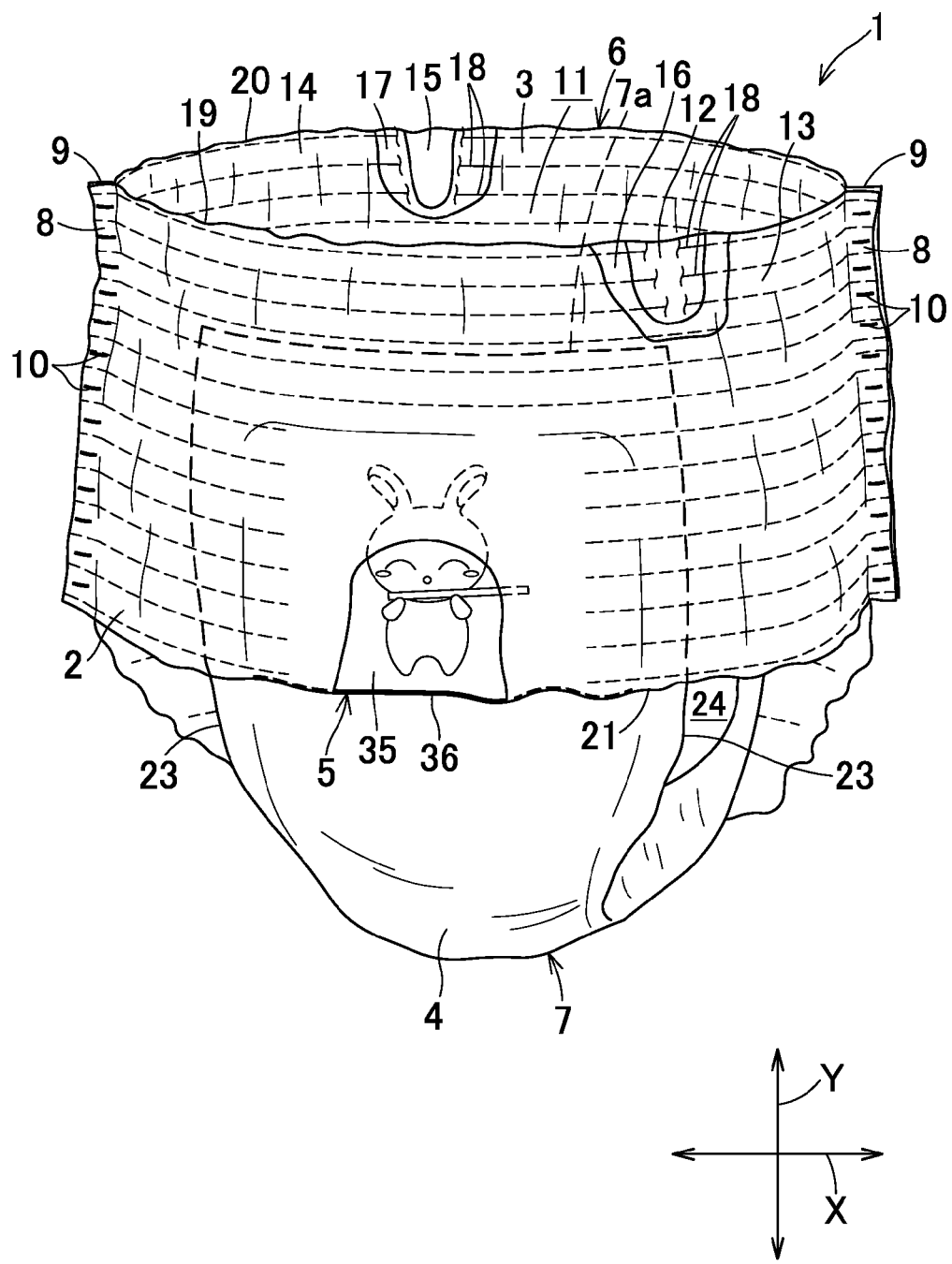
[FIG. 1] Perspective view of a diaper.

IDENTIFICATION OF REFERENCE NUMERALS USED IN THE DRAWINGS 1 diaper
5 front waist belt member
6 rear waist belt member
7 crotch member
12 inner sheet
13 outer sheet
14 inner sheet
15 outer sheet
16 heat-sealable sheet
17 heat-sealable sheet
18 waist elastic members
19 front waist line defining end
20 rear waist line defining end
21 end of front waist belt member lying on the side of crotch region
27 liquid-absorbent structure
35 non-contractile region
36 joint zones

DETAILED DESCRIPTION OF THE PREFERRED EMBODIMENTS

The present invention will be described in more details on the basis of a disposable diaper as one example of the wearing article with reference to the accompanying drawings.

FIG. 1 illustrates a pull-on-type diaper 1 as put on the wearer's body and partially cutaway for convenience of illustration. As illustrated, the diaper 1 comprises a front waist region 2, a rear waist region 3 and a crotch region 4 extending between the front and rear waist regions 2, 3. A direction continuously extending from the front waist region 2 across the crotch region 4 to the rear waist region 3 is referred to as a longitudinal direction Y and a direction extending orthogonally to the longitudinal direction Y is referred to as a transverse direction X.

The front and rear waist regions 2, 3 are respectively formed by front and rear waist belt members 5, 6 and the crotch region 4 is formed by a crotch member 7.

The front and rear waist belt members 5, 6 respectively have a pair of front side edges 8 and a pair of rear side edges 9 each of these front and rear pairs of side edges 8, 9 being opposite in the transverse direction and extending in the longitudinal direction Y. These front and rear pairs of side edges 8, 9 are put flat and joined together in a plurality of joint streaks 10 arranged intermittently in the longitudinal direction Y along the respective side edges 8, 9 so as to form an annular waist-opening 11.

The front waist belt member 5 comprises an inner sheet 12 defining an inner side facing the wearer's skin, an outer sheet 13 defining an outer side facing the wearer's garment and a heat-sealable sheet 16 sandwiched between these inner and outer sheets 12, 13. The rear waist belt member 6 comprises an inner sheet 14 defining an inner side facing the wearer's skin, an outer sheet 15 defining an outer side facing the wearer's garment and a heat-sealable sheet 17 sandwiched between these inner and outer sheets 14, 15. The heat-sealable sheets 16, 17 are formed on the respective sides thereof facing the wearer's garment substantially in the respective middles in the transverse direction X with graphics which are visible through the outer sheets 13, 15, respectively.

Between the heat-sealable sheets 16, 17 and the inner sheets 12, 14, there are provided a plurality of waist elastic members 18. These waist elastic members 18 are spaced from each other in the longitudinal direction so as to extend in the transverse direction X and attached under tension to the inner sheets 12, 14 and/or the heat-sealable sheets 16, 17 by adhesive (not shown). The front and rear waist belt members 5, 6 respectively have front and rear waist line defining ends 19, 20 and ends 21, 22 lying on the side of the crotch region, and both pairs of ends are opposed in the longitudinal direction Y and extending in the transverse direction X. The waist elastic members 18 are laid in regions extending between the respective waist line defining ends 19, 20 and the ends 21, 22 lying on the side of the crotch region 4. More specifically, as seen in FIG. 1, the waist elastic members 18 seen in upper zones of these respective regions as viewed in the longitudinal direction Y extend along the waist line defining ends 19, 20 and the waist elastic members 18 seen in lower zones of these respective regions as viewed in the longitudinal direction Y extend along the ends 21, 22 on the crotch region 4. Therefore, the waist elastic members 18 are attached to the diaper 1 in regions extending between the respective waist line defining ends 19, 20 and the ends 21, 22 lying on the side of the crotch region 4. It should be noted here that none of the waist elastic members 18 is present in regions overlapping the graphics printed on the respective heat-sealable sheets 16, 17.

The crotch member 7 is interposed between the front and rear waist belt members 5, 6 to connect these front and rear waist belt members 5, 6 in the longitudinal direction Y. Specifically, a front end 7a of the crotch member 7 is joined to the front waist belt member 5 and a rear end 7b is joined to the rear waist belt member 6. With the front and rear waist belt members 5, 6 joined to the crotch member 7 in this manner, the respective ends 21, 22 of the front and rear waist belt members 5, 6 both lying on the side of the crotch member 7 cooperate with transversely opposite side edges 23 of the crotch member 7 to form a pair of leg-openings 24.

FIG. 2 is a plan view of the diaper 1 as the front and rear waist regions have been peeled off from each other at the joint streaks 10 and then the contractile force of the respective elastic members have been inactivated so as to develop and flatten the diaper 1 from the state illustrated by FIG. 1. It should be appreciated that FIG. 2 is partially cut away for convenience of illustration. FIG. 3 is a sectional view taken along the line III-III in FIG. 2. As will be apparent from FIG. 2, the outer sheet 13 of the front waist belt member 5 is folded back onto the side facing the wearer's skin along the waist line defining end 19 to form a turnback region 25. The turnback region 25 covers the front end 7a of the crotch member 7. In the similar manner, the outer sheet 15 of the rear waist belt member 6 also is folded back along the waist line defining end 20 so as to form a turnback region 26 and to cover the rear end 7b of the crotch member 7.

The crotch member 7 includes a liquid-absorbent structure 27. The liquid-absorbent structure 27 comprises a liquid-absorbent core 28 formed from, for example, a mixture of fluff pulp and super-absorbent polymer particles, a liquid-absorbent/dispersant sheet 29 such as tissue paper adapted to wrap the core 28, a liquid-pervious liner 30 adapted to cover the liquid-absorbent/dispersant sheet 29 on the side of facing the wearer's skin, and an bottom sheet 31 adapted to cover the liquid-absorbent/dispersant sheet 29 on the side of facing the wearer's garment. Between the side facing the wearer's garment of the liquid-absorbent/dispersant sheet 29 and the bottom sheet 31 facing the wearer's garment, there is further a leak-barrier sheet 32 formed of a moisture-pervious plastic film. The leak-barrier sheet 32 has the size same as or larger than that of the core 28 and functions to prevent bodily fluids once absorbed by the core 28 from leaking out. The crotch member 7 which includes the liquid-absorbent structure 27 is covered on the front and rear ends 7a, 7b with the turnback regions 25, 26 of the outer sheets 14, 15, so as to prevent the core 28 from falling out from the liquid-absorbent structure 27.

Between the liner 30 facing the wearer's skin and the bottom sheet 31 facing the wearer's garment, a plurality of leg elastic members 33 extend in the longitudinal direction Y and attached under tension.

The core 28 and the liquid-absorbent/dispersant sheet 29 convexly bow inward in the transverse direction X substantially about middles thereof as viewed in the longitudinal direction Y so that the diaper 1 would fit around the wearer's legs when the diaper 1 is put on the wearer's body. With the diaper 1 put on the wearer's body, the liner 30 facing the wearer's skin and the bottom sheet 31 facing the wearer's garment both extending outward in the transverse direction X from the core 28 are lifted toward the wearer's skin to form a leak-barrier wall. Alternatively, leak-barrier cuffs may be separately provided on the crotch member 7 on the side of facing the wearer's skin to form the leak-barrier wall.

As will be apparent from FIG. 1, in the diaper 1 as has been described above, the front and rear waist belt members 5, 6 are provided with the waist elastic members 18 extending in the longitudinal direction X and none of these waist elastic members 18 overlaps the regions of the respective heat-sealable sheets in which the graphics are formed. In other words, the regions in which the graphics are formed are free from the contractile force of the waist elastic members 18. In this way, non-contractile regions 35 upon which the contractile force of the waist elastic members 18 are not exerted are defined.

The non-contractile regions 35 are formed by leaving the middles of the front and rear waist belt members 5, 6 in the transverse direction X not coated with adhesive between the inner and outer sheets 12, 13 as well as between the inner and outer sheets 14, 15 and cutting the waist elastic members 18 attached under tension in these middle regions. More specifically, the inner and outer sheets 12, 13 as well as the inner and outer sheets 14, 15 are coated with adhesive in the vicinity of the waist line defining ends 19, 20 and in the vicinity of the side edges 8, 9 of the front and rear waist belt members 5, 6 but left not coated with adhesive in the middles in the transverse direction X and in the vicinity of the ends 21, 22 on the side of the crotch member 7 so as to form the non-contractile regions 35.

The inner and outer sheets 12, 13 as well as the inner and outer sheets 14, 15 are not bonded to each other with adhesive in these non-contractile regions 35 also along the ends 21, 22 on the side of the crotch member 7. As for the ends 21, 22 of the front and rear waist belt members 5, 6 on the side of the crotch member 7, the inner and outer sheets 12, 13 as well as the inner and outer sheets 14, 15 are respectively heat sealed together so as to form a joint zone 36.

In the case of the diaper 1 provided with the non-contractile regions 35 as have been described above, these non-contractile regions 35 would not have stiffness increased since these regions 35 are not coated with adhesive. In consequence, desirable softness can be maintained for the wearer. Furthermore, the contractile force of the waist elastic members 18 is not exerted on these non-contractile regions 35 and therefore these regions 35 can be prevented from getting wrinkles. Without getting wrinkles, desired visibility of the graphics would not be disturbed. In addition, the liquid-absorbent structure 27 is placed on and bonded to the non-contractile regions 35 so that the contractile force of the waist elastic members 18 is not exerted also on the liquid-absorbent structure 27 which is, therefore, substantially prevented from getting wrinkles. In consequence, leak of bodily fluids due to wrinkles of the liquid-absorbent structure 27 can be prevented.

The ends 21, 22 of the respective non-contractile regions 35 on the side of the crotch member 7 are formed with the joint zones 36 and the inner and outer sheets 12, 13 as well as the inner and outer sheets 14, 15 would not open toward the crotch region 4. In this way, one or more of the ends of the waist elastic members 18 cut in the non-contractile regions 35 can be prevented from sticking out from between the inner and outer sheets 12, 13 and from between the inner and outer sheets 14, 15. Also, the wearer's skin can be prevented from being caught between these inner and outer sheets 12, 13; 14, 15.

As one of problems to be solved, the waist elastic members 18 must be at least partially attached also along the ends 21, 22 of the respective waist belt members 5, 6 on the side of the crotch member 7 and if the inner and outer sheets 12, 13; 14, 15 open toward the crotch member 7, particularly these elastic members 18 extending along these ends 21, 22 would otherwise be apt to stick out from between these sheets. However, such problem can be solved by forming the joint zones 36. As another problem to be solved, in order to form the non-contractile regions 35, these ends 21, 22 must be at least partially left not coated with adhesive when the waist elastic members 18 are attached along these ends 21, 22 and it would otherwise cause these ends to open toward the crotch member 7. However, undesirable opening of these ends 21, 22 can be effectively prevented by forming the joint zones 36.

The waist elastic members 18 attached along the ends 21, 22 of the front and rear waist belt members 5, 6 on the side of the crotch member 7 may be cut to form the non-contractile regions 35 and thereby to prevent boundaries with crotch member 7 from getting wrinkles. Consequently, a decrease of joint strength due to the wrinkles can be avoided when the front and rear waist belt members 5, 6 are joined to the crotch member 7 along the boundaries with the crotch member 7. In addition, should the boundaries with the crotch member 7 get wrinkles, these wrinkles would be unsightly distinct in contrast with the crotch member 7. This problem also can be overcome according to the present invention.

The waist elastic members 18 are attached along the ends 21, 22 of the front and rear waist belt members 5, 6 for a reason that the diaper 1 can be kept thereby fit to the wearer's body also along the ends of the front and rear waist belt members 5, 6 on the side of the crotch member 7 and thereby bodily fluids such as urine can be prevented from leaking out. It is also for the reason that strength of the ends 21, 22 of the front and rear waist belt members 5, 6 on the side of the crotch member 7 can be thereby increased. While the ends 21, 22 of the front and rear waist belt members 5, 6 are apt to be exposed to friction with the wearer's skin and the wearer's garment, the waist elastic members 18 attached also along these ends 21, 22 protect these ends 21, 22 from being broken due to such friction. The waist elastic members 18 attached along the ends 21, 22 of the front and rear waist belt members 5, 6 are arranged preferably to extend from the ends 21, 22 toward the waist line defining ends 19, 20 approximately by 15 mm or less.

The non-contractile regions 35 can be easily formed merely by cutting the waist elastic members 18 attached under tension. In this way, operation of forming the non-contractile regions 35 is neither difficult nor complicated even after the waist elastic members 18 have been attached along the ends 21, 22 on the side of the crotch member 7 because the regions 35 can be formed merely by cutting these elastic members 18.

The heat-sealable sheets 16, 17 sandwiched between the inner and outer sheets 12, 13 as well as between the inner and outer sheets 14, 15 make it unnecessary to coat any adhesive between these sheets 12, 13; 14, 15 and the joint zones 36 can be easily formed. It should be noted here that the means to form the joint zones 36 is not limited to the heat-sealing but an ultrasonic sealing technique or coating of appropriate adhesive may be used to form the joint zones between the inner and outer sheets 12, 13; 14, 15, respectively.

Both the front and rear waist belt members 5, 6 are formed in middle zones thereof with the graphics so that these graphics are visible through the front and rear waist regions 2, 3. However, it should be appreciated that such graphic may be formed in only one of the waist regions 2, 3 or none of such graphics may be formed in both waist regions 2, 3. While the non-contractile regions 35 are formed in the front and rear waist belt members 5, 6 in association with formation of the graphics in the case of the illustrated embodiment, the non-contractile region 35 may be formed in only one of the front and rear waist belt members 5, 6 or the non-contractile regions 35 may be formed whether the graphics are formed or not.

The joint zones 36 are preferably formed over ranges extending from the ends 21, 22 of the respective waist belt members 5, 6 on the side of the crotch member 7 toward the waist line defining ends 19, 20 of the respective waist belt members 5, 6 by about 10 mm or less, respectively. By dimensioning the respective joint zones 36, it is possible to reduce areas in which the inner and outer sheets 12, 13 as well as the inner and outer sheets 14, 15 are free from each other in the vicinity of the ends 21, 22 of the waist belt members 5, 6 on the side of the crotch member 7.

While the ends 21, 22 of the waist belt regions 5, 6 are formed on the side of the crotch member 7 according to the illustrated embodiment, the joint zones 36 also may be formed along the waist line defining ends 19, 20 when the non-contractile regions 35 are formed along the waist line defining ends 19, 20.

While the present invention has exemplarily been described on the basis of the pull-on-type diaper, the present invention is applicable also to open-type diapers.

The invention claimed is:

1. A wearing article having a longitudinal direction (Y), a transverse direction (X), comprising:
    an inner side facing the wearer's skin;
    an outer side facing a wearer's garment;
    a front waist region;
    a rear waist region;
    a crotch region extending between said front and rear waist regions and being contiguous one to another in said longitudinal direction;
    waist belt members defining said front and rear waist regions, respectively, and
    a crotch member defining said crotch region partially inclusive of said front and rear waist regions, wherein
    said waist belt members include a pair of waist line defining ends and a pair of ends on a side of said crotch member both pairs extending in said transverse direction and opposed to each other in said longitudinal direction,
    said waist belt members further include a plurality of waist elastic members provided under tension and extending in said transverse direction and spaced one from another in said longitudinal direction and said waist belt members are partially formed with non-contractile regions free from contractile force of said waist elastic members, each of said waist belt members includes an inner sheet defining an inner side facing said wearer's skin and an outer sheet defining an outer side facing said wearer's garment and said waist elastic members being interposed between said inner and outer sheets, said non-contractile regions is formed along at least said waist line defining ends of said waist belt members or said ends of said waist belt members on said side of said crotch member;

said inner and outer sheets are not bonded to each other in said non-contractile regions; and said waist line defining ends of said waist belt members and said ends of said waist belt members on said side of said crotch member both formed with said non-contractile regions are formed with joint zones along which said inner and outer sheets are joined together.

2. The wearing article according to claim 1, wherein said non-contractile regions are formed in regions in which said waist belt members overlap said crotch member.

3. The wearing article according to claim 2, wherein said waist belt members include heat-sealable sheets sandwiched between said inner and outer sheets, respectively, and said joint zones are formed by heat-sealing of said heat-sealable sheets.

4. The wearing article according to claim 3, wherein said waist elastic members partially extend along said ends of said waist belt members on said side of said crotch member, said non-contractile regions are defined along said ends of said waist belt members on said side of the crotch member, and said waist elastic members are cut in said non-contractile regions.

5. The wearing article according to claim 3, wherein said heat-sealable sheets are formed with graphics on a side facing the wearer's garment so as to make said graphics clearly visible through said outer sheets of said non-contractile regions.

6. The wearing article according to claim 5, wherein said waist elastic members partially extend along said ends of said waist belt members on said side of said crotch member, said non-contractile regions are defined along said ends of said waist belt members on said side of the crotch member, and said waist elastic members are cut in said non-contractile regions.

7. The wearing article according to claim 2, wherein said waist elastic members partially extend along said ends of said waist belt members on said side of said crotch member, said non-contractile regions are defined along said ends of said waist belt members on said side of the crotch member, and said waist elastic members are cut in said non-contractile regions.

8. The wearing article according to claim 1, wherein said waist belt members include heat-sealable sheets sandwiched between said inner and outer sheets, respectively, and said joint zones are formed by heat-sealing of said heat-sealable sheets.

9. The wearing article according to claim 8, wherein said heat-sealable sheets are formed with graphics on a side facing the wearer's garment so as to make said graphics clearly visible through said outer sheets of said non-contractile regions.

10. The wearing article according to claim 9, wherein said waist elastic members partially extend along said ends of said waist belt members on said side of said crotch member, said non-contractile regions are defined along said ends of said waist belt members on said side of the crotch member, and said waist elastic members are cut in said non-contractile regions.

11. The wearing article according to claim 8, wherein said waist elastic members partially extend along said ends of said waist belt members on said side of said crotch member, said non-contractile regions are defined along said ends of said waist belt members on said side of the crotch member, and said waist elastic members are cut in said non-contractile regions.

12. The wearing article according to claim 1, wherein said waist elastic members partially extend along said ends of said waist belt members on said side of said crotch member, said non-contractile regions are defined along said ends of said waist belt members on said side of the crotch member, and said waist elastic members are cut in said non-contractile regions.

13. The wearing article according to claim 1, wherein said crotch member includes a liquid-absorbent structure.

* * * * *